United States Patent [19]
Fischer et al.

[11] Patent Number: 5,869,617
[45] Date of Patent: Feb. 9, 1999

[54] HIGH AND LOW MOLECULAR WEIGHT FRACTIONS OF VON WILLEBRAND FACTOR AND PREPARATIONS OF SAME

[75] Inventors: Bernhard Fischer, Vienna; Artur Mitterer, Orth Donau; Friedrich Dorner, Vienna, all of Austria

[73] Assignee: Immuno Aktiengesellschaft, Vienna, Austria

[21] Appl. No.: 538,889

[22] Filed: Oct. 4, 1995

[30] Foreign Application Priority Data

Oct. 4, 1994 [DE] Germany .......................... 44 35 392.8

[51] Int. Cl.$^6$ .................................................. A61K 35/14
[52] U.S. Cl. .......................... 530/381; 530/383; 530/413; 514/8; 514/21
[58] Field of Search .................... 530/381, 383, 530/413; 514/8, 21

[56] References Cited

U.S. PATENT DOCUMENTS

| | | | |
|---|---|---|---|
| 5,198,349 | 3/1993 | Kaufman | 435/69.6 |
| 5,408,039 | 4/1995 | Burnouf-Radosevich et al. | 530/383 |
| 5,506,341 | 4/1996 | Newman et al. | 530/383 |

FOREIGN PATENT DOCUMENTS 0 383 234   8/1990   European Pat. Off. .

OTHER PUBLICATIONS

Wagner et al., "Inhibition of Disulfide of von Willerbrand Protein by Monensin Results in Small, Functionally Defective Multimers", J. Cell Biol., vol. 101, pp. 112–120, Jul. 1985.

Senogles et al., "von Willerbrand Factor A protein which binds at the cell Surface Interface between Platelets", J. Biol. Chem., vol. 258, No. 20, pp. 12327–12333, Oct. 1983.

Aihara et al., "Two Affinity Immunoelectrophoretic Methods for studying Collagen Interaction with von Willerbrand Factor Antigen", Tohoku J. exp. Med. 1987, vol. 153, pp. 169–177, Aug. 1987.

Baillod et al., "Multimeric Analysis of von Willerbrand Factory by Vertical Sodium Dodecyl Sulphate Agarose Gel Electrophoresis, Vacuum Blotting Technology and Sensitive Visualization by alkaline Phosphatase Anti–Alkaline Phosphatase Complex", Throm. Res. vol. 66, pp. 745–755, 1992.

Bradford, "A Rapid and Sensitive Method for the Quantitation of Microgram Quantities of Protein Utilizing the Principle of Protein–Dye Binding", Anal. Biochem., vol. 72, pp. 248–254, 1976.

Falkner et al., "High Level Expression of Active Human Prothrombin in a Vaccina Virus Expression System", Throm., vol. 68, No. 2, pp. 119–124, 1992.

Barrett et al., "Large–Scale Production and Purification of a Vaccinia Recombinant–Derived HIV–1 gp160 and Analysis of Its Immunogenicity", Aids Res. and Human Retroviruses, vol. 5, No. 2, 1989.

Laemmli, "Cleavage of Structural Proteins during the Assembly of the Head of Bacteriophage T4", Nature vol. 227, pp. 680–685, Aug. 15, 1970.

Furlan et al., "Triplet structure of von Willerbrand factor reflects proteolytic degradation of high molecular weight multimers", Proc. Natl. Acad. Sci. USA, vol. 90, pp. 7503–7507, Aug. 1993.

Mannheim, Translation of relevant part of Witt Biochemistry of Blood Coagulation and Fibrinolysis, pp. 14–16, 1991.

Putney, AIDS Vaccine and Research and Clinical Trials pp. 219–239, 1990.

Primary Examiner—Robert A. Wax
Assistant Examiner—Enrique D. Longton
Attorney, Agent, or Firm—Foley & Lardner

[57] ABSTRACT

The invention provides high and low molecular weight fraction of von Willebrand Factor (vWF), which can be obtained by absorbing vWF to a heparin affinity support followed by eluting the vWF at differing salt concentrations The low molecular weight fraction is predominantly dimers and tetramers, and the high molecular weight fraction is predominantly larger multimers.

19 Claims, 8 Drawing Sheets

Lane a:   Starting material of vWF
Lane b:   Eluate with 160 mM NaCl
Lane c:   Eluate with 270 mM NaCl

| LANE NUMBER: 38 | | TOTAL AREA: | 181 497 INCREMENTS | | |
|---|---|---|---|---|---|
| 1 = 84.3% | 0.0 g/l | 152 978 Inc | 0.60 Ext. | 20.7 mm |
| 2 = 14.9% | 0.0 g/l | 27 075 Inc | 0.17 Ext. | 26.4 mm |
| 3 = 0.4% | 0.0 g/l | 754 Inc | 0.01 Ext. | 32.8 mm |
| 4 = 0.4% | 0.0 g/l | 690 Inc | 0.02 Ext. | 78.1 mm |

| LANE NUMBER: | TOTAL AREA: | 204 155 | INCREMENTS |
|---|---|---|---|
| 1 = 41.3% | 84 314 Inc | 0.36 Ext. | 20.6 mm |
| 2 = 22.5% | 46 062 Inc | 0.26 Ext. | 26.1 mm |
| 3 = 10.8% | 21 966 Inc | 0.16 Ext. | 30.9 mm |
| 4 = 8.2% | 16 543 Inc | 0.14 Ext. | 34.5 mm |
| 5 = 5.2% | 10 550 Inc | 0.09 Ext. | 38.3 mm |
| 6 = 3.0% | 6 058 Inc | 0.07 Ext. | 41.6 mm |
| 7 = 2.8% | 5 799 Inc | 0.06 Ext. | 44.8 mm |
| 8 = 1.9% | 3 781 Inc | 0.05 Ext. | 47.5 mm |
| 9 = 1.8% | 3 709 Inc | 0.05 Ext. | 50.4 mm |
| 10 = 1.3% | 2 736 Inc | 0.03 Ext. | 52.8 mm |
| 11 = 0.4% | 839 Inc | 0.01 Ext. | 54.8 mm |
| 12 = 0.3% | 554 Inc | 0.01 Ext. | 56.9 mm |
| 13 = 0.6% | 1 144 Inc | 0.02 Ext. | 58.8 mm |

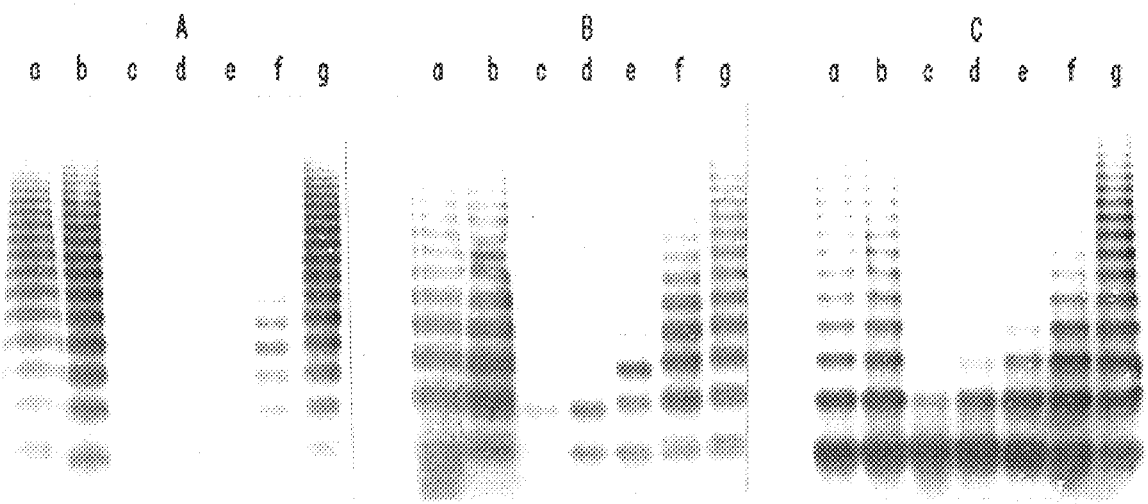

FIG. 7

Lane a. vWF before purification
Lane b. Eluate with 280 mM NaCl from Fraktogel EMD-TMAE
Lane c. Eluate with 120 mM NaCl after heparin affinity chromatography
Lane d. Eluate with 160 mM NaCl after heparin affinity chromatography
Lane e. Eluate with 190 mM NaCl after heparin affinity chromatography
Lane f. Eluate with 230 mM NaCl after heparin affinity chromatography
Lane g. Eluate with 280 mM NaCl after heparin affinity chromatography SDS-agarose gel electroporesis of p-vWF (a) and r-vWF (b) after afinity chromatography and elution with 280 NaCl.

HIGH AND LOW MOLECULAR WEIGHT FRACTIONS OF VON WILLEBRAND FACTOR AND PREPARATIONS OF SAME

DESCRIPTION

The invention relates to a method for fractionation of von Willebrand Factor into a high molecular and low molecular fraction.

Further, the invention relates to a low molecular fraction of von Willebrand Factor (vWF) molecules, a high molecular fraction of von Willebrand Factor molecules as well as a mixture of vWF molecule; of the low molecular and high molecular fraction.

BACKGROUND OF THE INVENTION

Direct and indirect functions are assigned to von Willebrand Factor in normally proceeding blood coagulation. It binds to Factor VIII in a complex. This complex serves to stabilize Factor VIII. This stabilized Factor VIII then has essential cofactor function in the activation of Factor X. Additionally, von Willebrand Factor directly influences blood coagulation by mediating platelet aggregation to injured vessels.

In plasma, vWF circulates in a concentration of 5–10 mg/l in the form of a non-covalent complex with Factor VIII. vWF is a glycoprotein which is formed in different cells of the human body and is later released into the circulation. Moreover, starting from a polypeptide chain with a molecular weight of about 220,000 (vWF monomer), a vWF diner (primary dimer) with a molecular weight of about 550,000 is made in cells by the formation of several sulfur bridges. Then, further polymers of vWF with increasing molecular weights up to about 20 million are produced from the vWF dimers by association.

There are several clinical pictures which are traceable to under- or overproduction of von Willebrand Factor. Thus, for example, an overproduction of vWF leads to an increased tendency towards thromboses, whereas an undersupply of vWF results in an increased bleeding tendency or prolonged bleeding time.

von Willebrand Syndrome can manifest itself in several forms. All forms are distinguished by a prolonged bleeding time which is based on either an absolute absence of a functional vWF or an abnormal spectrum in the multimer composition of vWF. Forms of von Willebrand disease in which multimer formation is reduced as well as forms in which low molecular vWF molecules are barely present are diagnosed thereby. Although other forms demonstrate high and low molecular vWF molecules, their concentration and/or their ratio to each other is drastically decreased and/or altered compared to a healthy person.

The lack of vWF can also cause hemophilia A because vWF, as mentioned above, is an essential component of functional Factor VIII. In these cases, the half-life of Factor VIII is decreased in such a manner that it can not fulfill its special functions in the blood coagulation cascade.

All forms of von Willebrand Syndrome as well as the form of hemophilia traceable to the lack of vWF were treated up to now by replacement of the missing vWF through intravenous infusions with concentrates of blood plasma which contain either vWF-Factor VIII complex or enriched vWF. Although in one respect the administration of Factor VIII is not necessary in both disease cases, the preparative separation of vWF from Factor VIII is technically very difficult to impossible.

In order to establish the exact function of high molecular vWF molecules on the one hand and low molecular vWF molecules on the other hand, ways have been looked for to isolate these fractions in enriched form. Wagner, D. D. et al (J. Cell Biol. 101: 112, 1985) prevent multimer formation by addition of monensin in vitro and conclude from different experiments that the low molecular form of vWF is not functional. On the other hand, Senogles, S. E. et al (J. Biol. Chem. 258: 12327, 1983) find no functional difference in ristocitin mediated platelet aggregation in high molecular and low molecular forms of vWF. They obtain low molecular forms by reduction of the sulfur bridges of high molecular vWF molecules. Aihara, M. et al (Tohoku J. Exp. Med. 153: 169, 1985) observe a lower binding capacity of vWF molecules from patients with von Willebrand Syndrome of the type IIa to collagen in affinity chromatography. This type of von Willebrand Syndrome is characterized by absence of the high molecular molecules of vWF.

In the literature, there are numerous methods which describe an analytical separation of high molecular and low molecular forms of von Willebrand Factor such that statements can be made as to the quantitative proportion of both forms. As an example, a publication from Baillod et al in Thrombosis Res. 66: 745, 1992 should be mentioned here. However, a preparative method for the separation of low molecular and high molecular forms has not been described to date.

SUMMARY OF THE INVENTION

The object of the present invention is to develop a preparative method for the fractionation of von Willebrand Factor (vWF) into a high molecular and low molecular fraction of von Willebrand Factor.

This object is solved by a method for the separation of vWF, especially of recombinant von Willebrand Factor, into high molecular vWF and low molecular vWF which is characterized in that vWF is bound to an affinity support and then eluted by different salt concentrations.

Preferred embodiments include separation methods where the vWF to be separated is present in a plasma fraction enriched with vWF. Alternatively, the vWF to be separated is recombinant vWF which is present in a recombinant vWF concentrate from cell free culture supernatants of transformed cells.

The purified vWF can be fractionated into high molecular vWF and low molecular vWF. The separation of vWF into high molecular vWF and low molecular vWF preferably is performed in a $Ca^{2+}$-free buffer system. The low molecular vWF can be eluted at a lower salt concentration than high molecular vWF.

For example, vWF can be bound to the affinity support at a salt concentration <150 mM, low molecular aggregates of vWF are eluted at a salt concentration between 150 and 250 mM, preferably 160 mM, and thereafter, high molecular aggregates of vWF are eluted at a salt concentration of >250 mM, preferably $\geq 270$ mM. Soluble mono- and divalent salts can be used as salts. A preferred salt is NaCl.

The affinity support is preferably a support with Heparin bound thereto, preferably using AF-heparin Toyopearl® (Tosohaas), Heparin EMD-Fraktogel® (Merck) or Heparin Sepharose Fast Flow®. The buffer solutions disclosed herein can comprise buffer substances and optionally salt, and can be used as a buffer system for affinity chromatography. For example, a buffer solution comprising Tris/HCl buffer, phosphate buffer or citrate buffer, and optionally sodium chloride, can used as a buffer system. Preferably, the affinity chromatography is carried out in a pH range of 6.0 to 8.5, more preferably at a pH value of 7.4.

In a particularly preferred embodiment of the present invention, the separation is performed in a $Ca^{2+}$-free buffer system. In this manner, high molecular vWF fractions or high molecular rvWF fractions which possess a particularly high physiological activity can be obtained with good yield.

Further subject matter of the present invention is a low molecular fraction of vWF molecules which comprises dimers and tetramers, whereby the dimers and tetramers consist of identical vWF subunits. Additionally, the invention relates to a low molecular fraction of vWF molecules which is obtainable by separation of vWF into high molecular vWF and low molecular vWF with an affinity support through elution at different salt concentrations. Various parameters for undertaking such separation are described above.

Preferred embodiments include low molecular fractions of vWF molecules which comprises at least 83% dimers and maximally 16% tetramers and maximally 1% higher polymers. The low molecular fraction of vWF molecules can be free from platelet aggregating action. The low molecular fraction of vWF molecules can bind to Factor VIII, contribute to the stabilization of Factor VIII and positively influences the storage stability of Factor VIII. Preferably, the low molecular fraction of vWF molecules comprises plasmic vWF and/or recombinant vWF.

The present invention relates to a high molecular fraction of vWF molecules which has an at least 50%, preferably 60%, improved activity per µg protein in platelet aggregation compared with the physiological mixture of high molecular and low molecular vWF molecules. Additionally, the invention relates to a high molecular fraction of vWF molecules obtainable by separation of vWF into high molecular vWF and low molecular vWF with an affinity support through elution at different salt concentrations. Various parameters for undertaking such separation are described above. According to the invention, the activity per µg protein can be even further increased.

Preferred embodiments of the high molecular fraction are are plasmic vWF and/or recombinant vWF.

The invention further relates to a mixture of the low molecular fraction of vWF molecules described above and the high molecular fraction of vWF molecules described above in any mixture ratio.

A preferred mixture is a mixture ratio in which the portion of low molecular vWF is lower than 35% or higher than 45%.

The invention also relates to the use of the low molecular fraction of vWF molecules or the high molecular fraction of vWF molecules or a mixture thereof in any mixture ratio for the treatment of hemophilia A or different forms of von Willebrand Disease.

In view of the prior art, it was not predictable that the fractions obtainable according to a preparative separation method and/or their mixtures are suitable for the treatment of the diseases mentioned.

Subject matter of the invention is also a pharmaceutical composition which comprises the low molecular fraction of vWF molecules or the high molecular fraction of vWF molecules or a mixture thereof in any mixture ratio in a physiologically acceptable carrier.

A preferred composition comprises Factor VIII or functional deletion mutant of Factor VIII, wherein the vWF molecules of the high molecular fraction or the low molecular fraction or the mixture thereof stabilizes Factor VIII or functional deletion mutations of Factor VIII.

The method according to the invention is suitable in the same manner for plasmic as well as recombinant vWF (rvWF). The starting material for the separation of the high and low molecular fractions is either a vWF enriched plasma fraction or a cell-free culture medium after fermentation of animal cells from which recombinant vWF was isolated and pre-purified.

The vWF used for the separation can be pre-purified with the aid of any known method.

According to the method of the invention for the separation of vWF, and especially rvWF, into high molecular and low molecular fractions, vWF is bound to an affinity support and then eluted at different salt concentrations.

To obtain particularly high yields, the separation is carried out in a $Ca^{2+}$-free buffer system.

The low molecular vWF fractions can be eluted at a lower salt concentration than the high molecular vWF fractions.

Soluble mono- and divalent salts are useable for the elution. Preferably, NaCl is used. Calcium salts are not suitable for the elution.

In a preferred embodiment, vWF is bound to the affinity support at a salt concentration of <150 mM. At a salt concentration between 150 and 250 mM, and especially 160 mM, the low molecular aggregates of vWF are then eluted, and thereafter, at a salt concentration of >250 mM, and especially at >270 mM, the high molecular aggregates are eluted.

NaCl is prefer red as a salt. Calcium salts are not suitable.

The method according to the invention is preferably carried out on a heparin affinity chromatography column. Any support on which heparin can be bound can be used for the affinity chromatography. For example, AF-HEPARIN-TOYOPEARL® (a synthetic, large-pored, hydrophilic polymer based on methacrylate (Tosohaas), HEPARIN EMD-FRAKTOGEL® (a synthetic, hydrophilic polymer based on ethylene glycol, methacrylate and dimethylacrylate) (Merck) or HEPARIN SEPHAROSE FAST FLOW® (containing natural dextran and/or agarose derivatives) (Pharmacia) have demonstrated themselves as well suited.

The affinity chromatography is preferably performed in a pH range of 6.0 to 8.5, and especially at a pH value of 7.4.

In the method according to the invention, a buffer solution comprising buffer substances, especially Tris/HCl buffer, phosphate buffer or citrate buffer, and optionally salt, which is preferably free from stabilizers, amino acids and other additives is used as a buffer system. It was shown that a particularly good separation of low molecular and high molecular vWF protein aggregates can be achieved with a vWF solution treated with EDTA in a $Ca^{2+}$-free buffer system. Therefore, in this manner, high molecular vWF fractions or high molecular rvWF fractions which have a particularly high physiological activity can also be obtained with good yield.

In the method according to the invention, a recombinant vWF concentrate from cell-free culture supernatants of transformed cells is preferably employed.

According to the method of the invention for the separation of vWF into high molecular and low molecular fractions, low molecular and high molecular vWF can be obtained in an efficient and simple manner. Therefore, according to this separation method, the particularly physiologically active high molecular or low molecular fractions of vWF which are therewith exceptionally suitable for the treatment of hemophilia A and different forms of von Willebrand Disease can be produced with good yield.

In a preferred embodiment according to the invention, purified vWF is fractionated into high molecular vWF and low molecular vWF The vWF employed for the separation can be pre-purified with the aid of any known method.

Particularly preferred is the purified von Willebrand Factor obtainable according to a method which comprises the steps of chromatographically purifying plasmic von Willebrand Factor by an anion exchange chromatography on an anion exchanger of the quaternary amino type and an affinity chromatography on immobilized heparin in a buffer solution comprising buffer substances and optionally salt.

In a further preferred embodiment, the purified von Willebrand Factor is obtainable according to a method which comprises the steps of chromatographically purifying recombinant von Willebrand Factor by an anion exchange chromatography on an anion exchanger of the quaternary amino type and an affinity chromatography on immobilized heparin in a buffer solution comprising buffer substances and optionally sodium chloride.

Particularly preferred is the purified von Willebrand Factor obtainable according to a method in which a rvWF concentrate is purified from cell-free culture supernatants of transformed cells.

In the purification of vWF, a buffer system free from stabilizers, amino acids and other additives is particularly preferred as a buffer solution.

The anion exchange chromatography and/or the affinity chromatography is preferably carried out in a pH range of 6.0 to 8.5, and more preferably at a pH value of 7.4.

The von Willebrand Factor bound on the anion exchanger in anion exchange chromatography and on immobilized heparin in affinity chromatography can be eluted by increasing the salt concentration.

The quaternary anion exchanger of a Fraktogel with tentacle structure is preferred, especially an EMD-TMAE-Fraktogel.

In the purification method, the vWF on the anion exchanger is preferably bound at a salt concentration of $\leq 270$ mM NaCl and eluted at a salt concentration of >270 mM NaCl, and preferably >280 mM NaCl.

In the purification of vWF, affinity chromatography is preferably carried out on a support with heparin bound thereto, whereby preferably AF-HEPARIN TOYOPEARL® (Tosohaas), HEPARIN EMD-FRAKTOGEL® (Merck) and HEPARIN SEPHAROSE FAST FLOW® are equally suitable.

In a preferred embodiment, the purified von Willebrand Factor is obtainable according to a method in which the vWF, pre-purified in anion exchange chromatography, binds to the immobilized heparin at a salt concentration of <150 mM NaCl and is eluted at a salt concentration of >150 mM NaCl, preferably at 200 to 300 mM NaCl, more preferably 160 to 270 mM NaCl.

It is advantageous to employ previously purified concentrates as the starting material for the separation of high molecular and low molecular vWF. Additionally, the chromatographic separation method results in a further purification effect.

The high molecular and low molecular fractions obtained according to the separation method of the invention as well as mixtures of both fractions in any mixture ratio are physiologically active and can be employed for therapeutic purposes.

The low molecular fraction of vWF molecules is characterized in that it predominantly comprises diners and tetramers which consist of identical vWF subunits.

The portion of dimers and tetramers in the low molecular fraction is higher than in the physiological composition of vWF.

It was surprisingly found that low molecular fractions of recombinant vWF consist of identical vWF subunits, whereas fractions of plasmic vWF consist of a mixture of dimers and tetramers with different subunits.

The low molecular fraction of vWF molecules is obtainable according to a method described above.

In a preferred embodiment, the low molecular fraction of vWF molecules comprises at least 83% dimers and maximally 16% tetramers and maximally 1% higher polymers. The low molecular fraction is free from platelet aggregating action, binds Factor VIII, contributes to the stabilization of Factor VIII and positively influences the storage stability of Factor VIII.

The low molecular fraction of vWF molecules preferably consists of recombinant vWF.

The high molecular fraction of vWF molecules has an at least 50%, preferably 60%, improved activity per $\mu$g protein in platelet aggregation as compared with the physiological mixture of high molecular and low molecular vWF molecules.

The high molecular fraction of vWF molecules is obtainable according to a method described above.

It was surprisingly found that the high molecular fraction of recombinant vWF comprises multimers which consist of identical vWF subunits, whereas fractions of plasmic vWF consist of a mixture of multimers with different subunits.

The high molecular fraction of vWF molecules preferably consists of recombinant vWF.

Surprisingly, it was found that the low molecular as well as the high molecular fraction of recombinant vWF possess a potentially higher binding capacity to Factor VIII in comparison to corresponding fractions of plasmic vWF. Hence, the fractions of recombinant vWF bind Factor VIII more efficiently than the plasmic fractions.

The different use of the high molecular and/or low molecular fractions results from their physiological activity. The possibility of the production of purposive mixtures of both fractions permits the treatment of special medical indications.

Hence, further subject matter of the present invention is the use of the low molecular fraction of vWF molecules or the high molecular fraction of vWF molecules or a mixture thereof for the treatment of hemophilia A or different forms of von Willebrand Disease.

It is especially pointed out that when using recombinant vWF in the separation method according to the invention, the end products (high molecular and low molecular fractions as well as mixtures of both fractions in any mixture ratio) are free from plasma proteins and free from Factor VIII as well as free from pathogenic viruses. In the production of pharmaceutical products, as they are mentioned above, this can be of great advantage for certain medical indications.

Subject matter of the present invention is also a pharmaceutical composition which comprises the low molecular fraction of vWF molecules or the high molecular fraction of vWF molecules or a mixture thereof in any mixture ratio in a physiologically acceptable carrier.

Preferably, the pharmaceutical composition comprises Factor VIII or functional deletion mutation(s) of Factor VIII, whereby the vWF molecules of the high molecular fraction or the low molecular fraction or the mixture thereof stabilize Factor VIII or functional deletion mutation(s) of Factor VIII.

For the production of pharmaceutical preparations, the respective fractions or their mixtures are preferably concentrated and the concentrate is further processed.

The production of the pharmaceutical compositions can occur in a known and customary manner. Preferably, the products (low molecular and high molecular fractions as well as any possible mixture thereof) or the concentrates comprising these can be mixed with a suitable physiologically acceptable carrier. Preferably, a physiological sodium chloride solution serves as a carrier.

The pharmaceutical compositions can be present in an administration form customary and usual for the treatment of hemophilia A and different forms of von Willebrand Disease; preferably they are present in the form of a preparation suitable for infusion.

BRIEF DESCRIPTION OF THE FIGURES

FIG. 7 depicts an electrophoretic analysis of the fractions with different degrees of polymerization after separation of vWF multimers of p-vWF, K-vWF and r-vWF.

DETAILED DESCRIPTION OF PREFERRED EMBODIMENTS

In the following Examples, the invention is more closely illustrated without restricting the invention to the Examples.

In Example 1, the separation according to the invention of high molecular and low molecular vWF polymers by means of heparin affinity chromatography is shown.

Example 1: Separation of high and low molecular forms of von Willebrand Factor

Recombinant von Willebrand Factor (rvWF) in 20 mM Tris/HCl buffer (Tris buffer), pH 7.4, was applied to a glass column which was filled with AF-HEPARIN-TOYOPEARL® (Tosohaas) with a flow speed of 1 ml/min/cm$^2$. The column was first washed with Tris buffer in order to remove non-specifically bound proteins. Then, the column was eluted with 160 mM NaCl in Tris buffer and subsequently with 270 mM NaCl in Tris buffer. During the chromatography, the protein absorption was followed in a customary manner at 280 nm. After the chromatography, the protein concentration was determined by means of the Bradford method (M. Bradford, Anal. Biochem. 72: 248–254, 1976). The content of rvWF was determined by means of a commercial ELISA system (Boehringer Mannheim). The distribution of multimer structures of recombinant von Willebrand Factor in the individual purification fractions was examined by SDS agarose gel electrophoresis in the customary manner and quantitatively analyzed by densitometry. The capacity of ristocetin mediated blood platelet aggregation was examined by means of a commercial test system (von Willebrand Reagent, Behring Werke).

Figure 1:
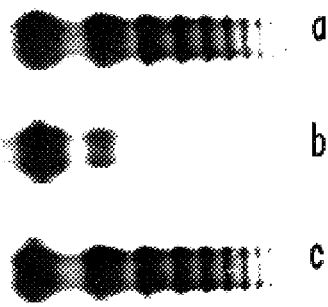
FIG. 1 depicts the multimer spectrum of individually obtained vWF from an SDS-agarose gel electrophoresis.

FIG. 1 shows the multimer spectrum of the individually obtained fractions. At a salt concentration of 160 mM NaCl, rvWF with low molecular weight, predominantly of the primary dimer type, was eluted. In contrast, rvWF with high molecular weight was eluted at a salt concentration of 270 mM NaCl.

Figure 2:
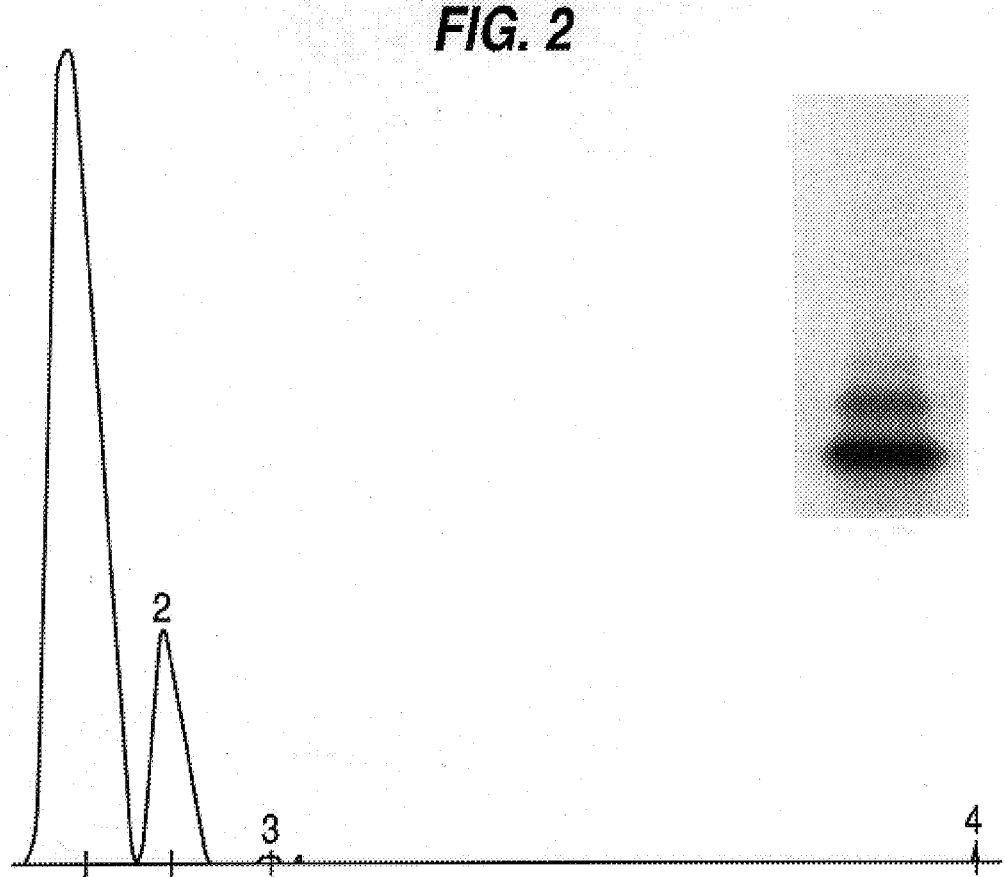
FIG. 2 depicts a densitometric analysis of the distribution of multimers of a recombinant vWF fraction obtained by elution with 160 mM NaCl.

FIG. 2 shows a densitometric analysis of the distribution of multimers of recombinant von Willebrand Factor obtained at 160 mM NaCl. This analysis demonstrated that the rvWF-polymer mixture obtained in this manner comprised up to 84.4% of the primary dimers (molecular weight about 440,000) and up to 14.9% of the tetramers (molecular weight about 880,000).

Figure 3:
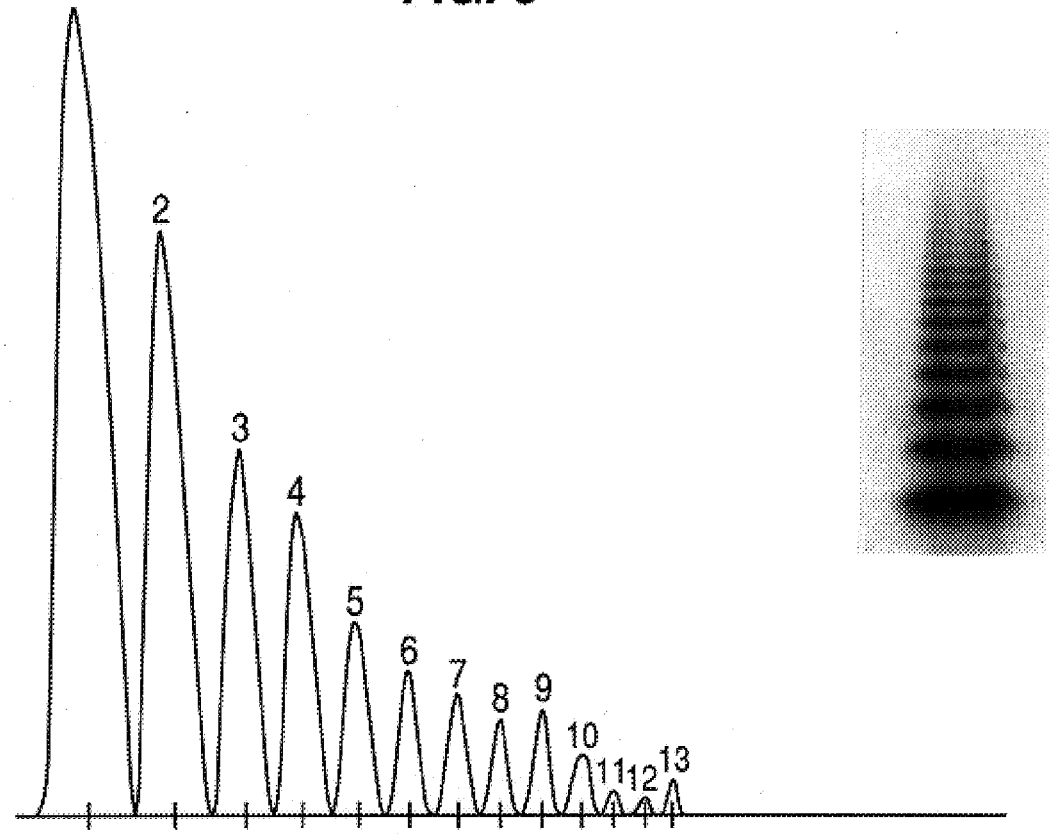
FIG. 3 depicts a densitometric analysis of the distribution of multimers of a recombinant vWF fraction obtained by elution with 270 mM NaCl.

A densitometric analysis of the rvWF fraction shown in FIG. 3 which was obtained by elution with 270 mM NaCl demonstrated that the rvWF-polymer mixture obtained in this manner comprises a cascade of increasingly higher polymers.

The results of the chromatography and the first functional analysis of rvWF fractions are compiled in Table 1. From the analysis it emerges that nearly the entire rvWF was bound to the support. The rvWF-polymer mixture eluted with 160 mM NaCl (low molecular) demonstrated no capacity for agglutination of blood platelets. The fraction eluted at 270 mM NaCl (high molecular) possessed a high activity with respect to platelet aggregation. By the fractionation of the non-aggregating, low molecular rvWF forms, the specific activity with respect to the agglutination was increased by 69% compared to the starting material.

At the same time, the purity of the rvWF was substantially increased by chromatography of the rvWF on the affinity support described in Example 1. rvWF of the 160 mM NaCl fraction showed a double, and rvWF of the 270 mM NaCl fraction a 6-fold, higher purity in comparison to the starting material.

TABLE 1

| Sample | Volume ml | Protein mg/ml | vWF:AG μg/ml | vWF:AG mg | μg vWF:AG/ μg Protein | Agglutination mU/μg Protein | Agglutination mU/μg vWF:AG |
|---|---|---|---|---|---|---|---|
| rvWF Start | 560 | 0.62 | 92 | 51 | 0.15 | 0.650 | 4.3 |
| 160 mM NaCl eluate | 98 | 0.2 | 54 | 6 | 0.27 | 0 | 0 |
| 270 mM NaCl eluate | 86 | 0.5 | 440 | 38 | 0.88 | 6.4 | 7.27 |

Example 2: Binding of recombinant von Willebrand Factor to Factor VIII

The following experiments were carried out in ELISA microtitration plates which were coated with anti-vWF immunoglobulin (Asserachrom vWF, Boehringer Mannheim). 5 ng of vWF respectively was coupled to the reaction container by 1 hour incubation at room temperature with 200 µl 50 mM Tris/HCl, pH 7.4, 150 mM NaCl, 0.5% albumin, 0.1% Tween 20 (TBS buffer) which contained 100 ng/ml vWF:AG. The following vWF samples were used: human vWF (Diagnostika Stago), rvWF (starting material from Example 1), low molecular rvWF(160 mM NaCl elution fraction from Example 1), high molecular rvWF (270 mM NaCl elution fraction from Example 1). The microtitration plates were subsequently washed 3 times for 3 minutes with TBS and subsequently each reaction container was covered with a layer of 25 µl recombinant Factor VIII (Miles) in TBS and incubated for 1 hour at room temperature. The concentration of Factor VIII was varied in the range of 100 mU/ml to 7.12 mU/ml. Thereafter, the reaction containers were washed 3 times for 3 minutes each with 200 µl TBS. Subsequently, the amount of Factor VIII bound by the immobilized vWF was determined by means of a commercial test system (Chromogenix Coatest VIII:C/4).

Figure 4:
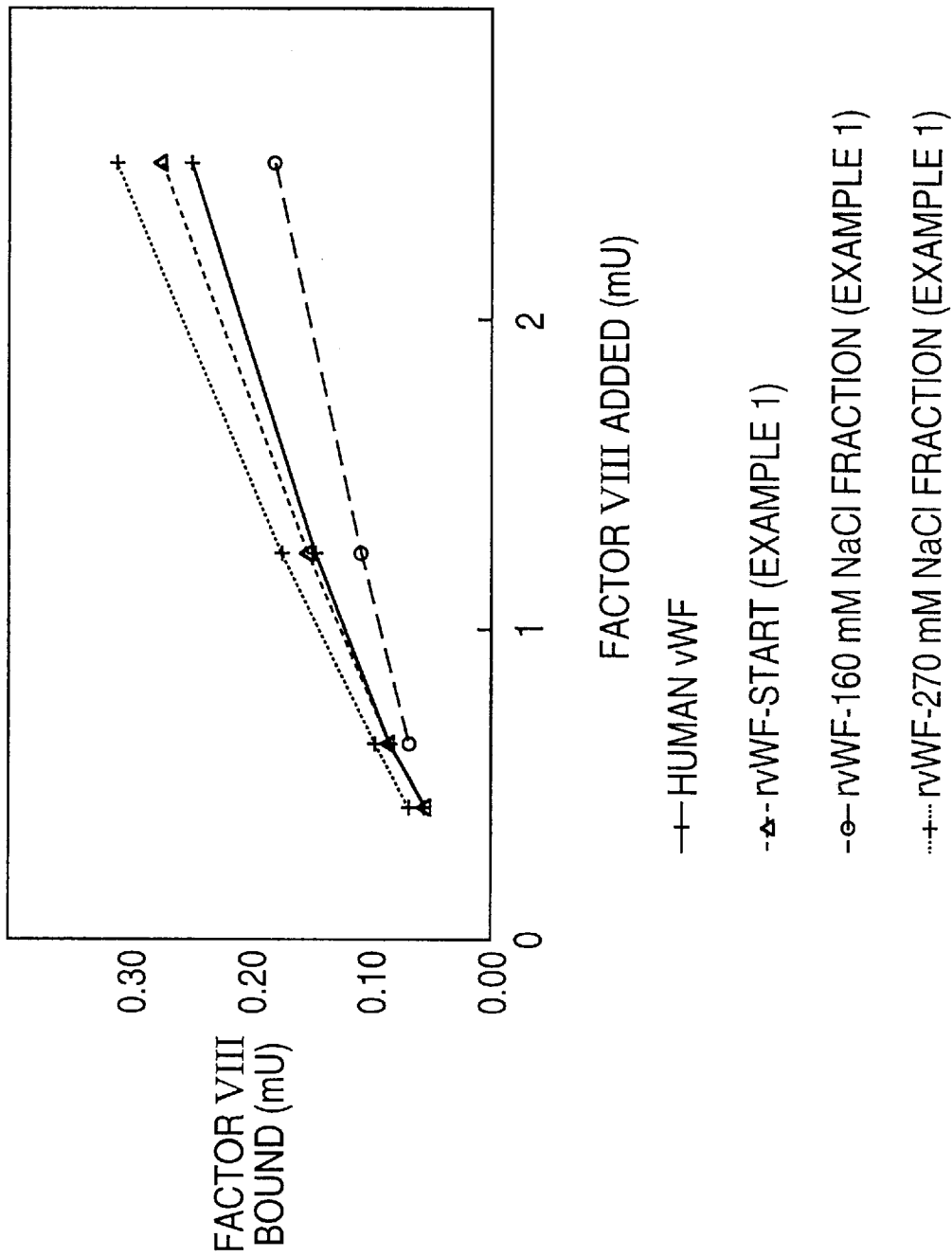
FIG. 4 depicts the binding of Factor VIII to von Willebrand Factor as a function of the available amount of Factor VIII.

FIG. 4 shows the binding of Factor VIII to von Willebrand Factor as a function of the available amount of Factor VIII. The results demonstrate that all examined vWF fractions bind Factor VIII in a concentration dependent manner, whereby rvWF demonstrated an approximately identical Factor VIII binding compared with human vWF. rvWF of the 270 mM NaCl fraction from Example 1 demonstrated an increased binding of Factor VIII; rvWF from the 160 mM NaCl fraction, an insignificantly lower binding of Factor VIII.

Example 3: Stabilization of recombinant Factor VIII by recombinant von Willebrand Factor Factor VIII is physiologically bound in the human body by von Willebrand Factor and is stable in this form. As opposed to this, unbound Factor VIII is proteolytically inactivated in a few minutes.

Different fractions of recombinant von Willebrand Factor obtained according to the method from Example 1 were added to transformed SK-Hep cells in cell culture which secrete Factor VIII. After 24 hours, the activities of recombinant Factor VIII in the cell culture supernatants were determined by means of a commercial test system (Chromogenix Coatest VIII:C/4). The results are compiled in Table 2. From the data, it is evident that a substantially higher concentration of Factor VIII was present after 24 hours by adding rvWF to the cells. The high molecular vWF fraction as well as the low molecular vWF fraction bind and stabilize Factor VIII, whereby the high molecular fraction has a better capacity for stabilizing Factor VIII than the low molecular fraction.

Additionally, these data demonstrate that recombinantly produced Factor VIII can also be stabilized by addition of von Willebrand Factor.

TABLE 2

| Sample 15 µg/ml | Factor VIII activity after 24 hours U/ml |
|---|---|
| control | 0.5 |
| rvWF start | 1.8 |
| rvWF-160 mM NaCl eluate | 0.8 |
| rvWF-270 mM NaCl eluate | 2.4 |

Example 4: Stabilization of Factor VIII by recombinant von Willebrand Factor

Mixtures of Factor VIII and recombinant von Willebrand Factor from cell culture supernatants, as they were obtained in Example 3, were frozen at –20° C. and kept for 6 days at –20° C. Thereafter, the activity of Factor VIII was determined again. Table 3 summarizes the results.

It is evident from the results that all tested vWF fractions increase the storage stability of Factor VIII more that 2.5-fold. This also indicates a strong binding of vWF-Factor complexes with the low molecular fractions.

TABLE 3

| Sample | Factor VIII activity (mU/ml) | | |
|---|---|---|---|
| 15 µg/ml | t = 0 | t = 6 days | % loss |
| control | 500 | 150 | 70 |
| rvWF start | 1800 | 1300 | 28 |
| rvWF-160 mM NaCl eluate | 800 | 600 | 25 |
| rvWF-270 mM NaCl eluate | 2400 | 1800 | 25 |

Example 5: Purification of rvWF from culture supernatants by anion exchange chromatography Recombinant vWF was isolated according to customary methods after infection of Vero cells (monkey kidney cells) with vaccinia virus in cell culture. Vero/vaccinia expression systems and cell culture conditions are described in detail in F. G. Falkner et al., Thrombosis and Haemostasis 68 (1992) 119–124, N. Barrett et al., AIDS Res. 5 (1989) 159–171 and F. Dorner et al., AIDS Vaccine Research and Clinical Trials, Marcel Dekker, Inc., New York (1990). The expression of vWF occurred in synthetic DMEM standard medium (Dulbeccos minimal essential medium).

After the fermentation of the transformed cells, the culture medium was fractionated and cells and cell fragments were removed by centrifugation. Additional smaller components such as membrane fragments or bacteria were removed by filtration through a filter with a pore size of 0.4 µm.

770 ml of cell-free culture supernatant was filtered over a column (1.6 cm×5 cm, filled with 10 ml of the anion exchanger EMD-TMAE-Fraktogel (Merck)) with a flow speed of 2 ml/cm$^2$/min. The gel was previously equilibrated with 20 mM Tris/HCl buffer (pH 7.4). Subsequently, the column was washed with 20 mM Tris/HCl buffer (pH 7.4). Foreign materials were removed by washing the column with buffer containing 200 mM NaCl. The rvWF was then eluted from the support with 280 mM NaCl in 20 mM Tris/HCl buffer (pH 7.4). Subsequently, any residual material present was eluted from the column with 1M NaCl. During chromatography, the protein absorption was followed at 280 nm in the customary manner. After chromatography, the protein concentration was determined according to the Bradford method (M. Bradford, Anal.

Biochem. 72 (1976) 248–254). The content of rvWF was determined by means of a commercial ELISA system (Boehringer Mannheim).

It was found that nearly the total rvWF was bound to the support. rvWF was eluted from the anion exchanger by 0.28M NaCl. The results of the purification of rvWF on the anion exchanger are summarized in Table 4.

rvWF was enriched 6-fold by the purification described in this Example.

TABLE 4

| Sample | volume (ml) | Total Protein (µg/ml) | rvWF (µg/ml) | rvWF/ total protein |
|---|---|---|---|---|
| cell-free culture supernatant | 770 | 113 | 7.9 | 0.069 |
| Elution with 200 mM NaCl | 95 | 147 | 0.0016 | 0.00001 |
| Elution with 280 mM NaCl | 75 | 168 | 61 | 0.36 |
| Elution with 1M NaCl | 50 | 196 | 6 | 0.03 |

Example 6: Purification of rvWF by affinity chromatography rvWF obtained according to Example 5 was diluted with 20 mM Tris/HCl buffer (pH 7.4) to decrease the salt concentration (160 mM NaCl). Subsequently, the solution was filtered through a column (1.6 cm×5 cm, filled with 10 ml of AF-HEPARIN-TOYOPEARL® 650 (Tosohaas)) with a flow speed of 1 ml/cm$^2$/min . The column was previously equilibrated with 20 mM Tris/HCl buffer (pH 7.4). Non-specifically bound proteins were first removed by washing with 20 mM Tris/HCl buffer (pH 7.4). rvWF was then eluted from the support by 270 mM NaCl in 20 mM Tris/HCl buffer (pH 7.4). Subsequently, residual material was eluted from the column with 1M NaCl. During chromatography, the protein absorption was followed at 280 nm in the customary manner. After chromatography, the protein concentration was determined according to the Bradford method (M. Bradford, loc.cit.). The content of rvWF was determined by means of a commercial ELISA system (Boehringer Mannheim).

It was found that nearly the total rvWF was bound to the support. The majority of rvWF was eluted from the column in the elution with 270 mM NaCl, while the wash with 1M NaCl only contained traces of rvWF. The results of this purification step are summarized in Table 5. The portion of rvWF protein to total protein was increased to over 86% by this purification step.

The fraction of 270 mM NaCl was more precisely examined with denaturing SDS protein gel electrophoresis (U. K. Laemmli, Nature 227 (1970) 680–685) and subsequent Western blot.

Figure 5:
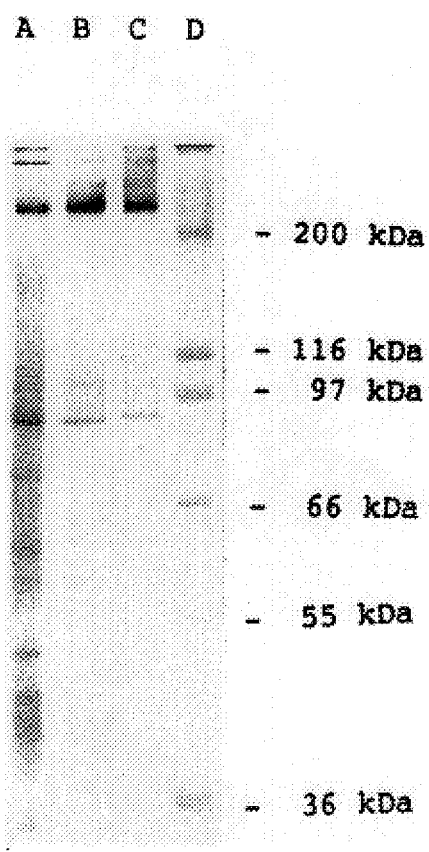
FIG. 5 depicts a denaturing electrophoretic analysis of the purified rvWF.

As presented in FIG. 5, the denaturing electrophoretic analysis established that rvWF was recovered at high purity by the purification described in Example 5 and Example 6. In the product isolated in this manner, no other coagulation factors, such as Factor VIII, could be detected.

TABLE 5

| Sample | volume (ml) | Total Protein (µg/ml) | rvWF (µg/ml) | rvWF/ total protein |
|---|---|---|---|---|
| rvWF concentrate | 225 | 50 | 13.9 | 0.27 |
| Elution with 270 mM NaCl | 43 | 70 | 60 | 0.86 |
| Elution with 1M NaCl | 32 | 25 | 2 | 0.08 |

Example 7: Isolation of plasmic and recombinant von Willebrand Factor with different multimerization and characterization of the binding to Factor VIII Recombinant von Willebrand Factor (r-vWF), von Willebrand Factor from human plasma (p-vWF) and von Willebrand Factor from plasma cryoprecipitate (k-vWF) were purified by a combination of anion exchange chromatography and heparin affinity chromatography.

In anion exchange chromatography, the starting material (r-vWF: fermentation supernatant of recombinant CHO cells; p-vWF: human citrate plasma; k-vWF: plasma cryoprecipitate) was applied on a Fraktogel-EMD-TMAE column (Merck) and vWF was obtained by elution with 20 mM Tris/HCl buffer, pH 7.0, 280 mM NaCl. Subsequently, the preparations were diluted to a salt concentration of 90 mM by addition of 20 mM Tris/HCl buffer and applied to a Fraktogel-EMD-heparin column (Merck). vWF was eluted by a stepwise elution with increasing salt concentration. Thereby, the NaCl concentration in 20 mM Tris/HCl buffer was varied between 120 mM and 280 mM. In this manner, preparations for p-vWF, k-vWF as well as r-vWF which differ from each other in the composition of multimers were obtained at 120 mM NaCl, 160 mM NaCl, 190 mM NaCl, 230 mM NaCl and 280 mM NaCl.

The content of vWF (vWF-antigen, vWF:Ag) was determined by means of a customary ELISA test (Asserachrom vWF, Boehringer Mannheim).

Figure 6:
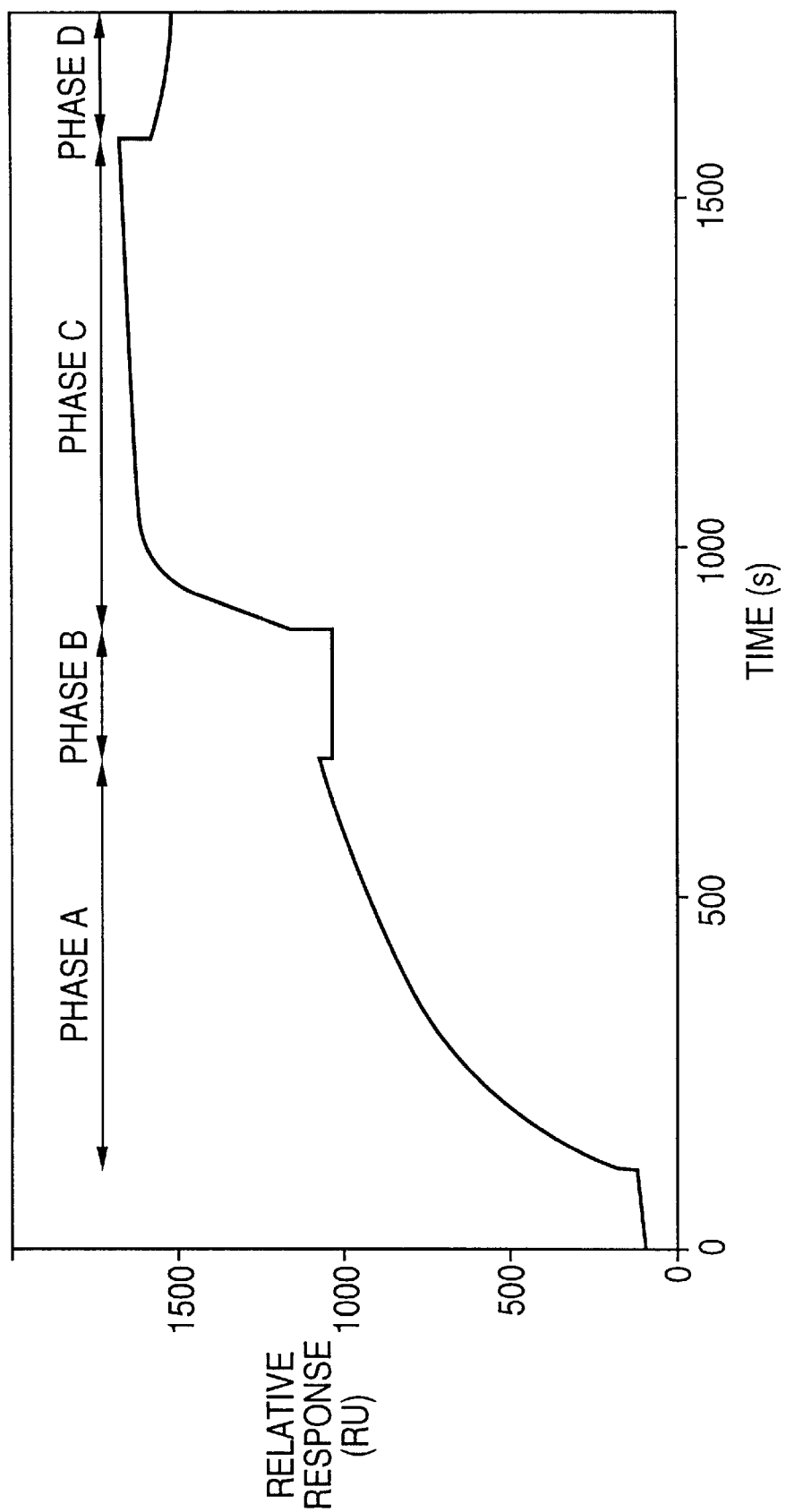
FIG. 6 depicts a sensogram of the attachment of r-Factor VIII to r-vWF, which shows the kinetics of the interaction between these factors.

The binding of coagulation Factor VIII to p-vWF, k-vWF as well as r-vWF was determined by means of "real-time biospecific interaction analysis" based on measurements from surface plasmon resonance technology (Malmqvist, M. Nature 1993; 361: 186–187). Thereby, the stochiometric ratio of vWF subunit to bound Factor VIII was determined: a monoclonal anti-human von Willebrand antibody (AvW8/2) was covalently bound to the sensorchip CM5 (Pharmacia Biosensor AB) (O'Shannessy, D. J. et al., 1993 Anal. Biochem. 212: 457–468; Karlsson, R. 1994 Anal. Biochem. 221: 142–151). Thereby, the measurement of resonance units (RU) corresponds to the baseline ($RU_{BL}$).

p-vWF, k-vWF and r-vWF were dissolved to a concentration of 20 µg/ml in 10 mM HEPES, pH 7.4, 150 mM NaCl, 1 mM $CaCl_2$, 0.05% surfactant P20 (HBS buffer). For each experiment, a 50 µl sample of vWF was applied over the sensorchip with a flow speed of 5 µl/min in order to permit the binding of AvW8/2 to vWF (phase A). Non-bound vWF is removed by washing with HBS buffer (phase B). p-vWF and k-vWF were additionally washed with 20 µl 250 mM $CaCl_2$ in order to remove traces of plasmic Factor VIII. The binding of vWF to AvW8/2 corresponds to the vWF resonance unit ($RU_{vWF}$). For the analysis of the binding of Factor VIII, 60 µl of recombinant FVIII (2.5 µg/ml in HBS buffer) was injected over the sensorchip at a constant flow rate of 5 µl/min in order to permit the binding of Factor VIII to the vWF (phase C). The measurement of the resonance units corresponds to the FVIII binding (RU$_{FVIII}$). Factor VIII was dissociated again from vWF by washing with HBS buffer (phase D). The stochiometric ratio of the complex of FVIII and vWF subunit is established from the resonance units and the molecular weights: vWF (subunit): FVIII=(RU$_{vWF}$−RU$_{BL}$)/(RU$_{FVIII}$−RU$_{vWF}$)×330,000 / 220,000 (O'Shannessy, D. J. et al., 1993 Anal. Biochem. 212: 457–468; Karlsson, R. 1994 Anal. Biochem. 221: 142–151). FIG. 6 shows the sensogram of the attachment of r-Factor VIII to r-vWF.

TABLE 6

Determination of the stochiometry of the vWF-Factor VIII complex

| Sample | Stochiometry vWF subunit: FVIII |
|---|---|
| r-vWF 120 mM eluate | 2.25:1 |
| r-vWF 160 mM eluate | 2.5:1 |
| r-vWF 190 mM eluate | 2.0:1 |
| r-vWF 230 mM eluate | 2.0:1 |
| r-vWF 280 mM eluate | 2.0:1 |
| k-vWF 280 mM eluate | 2.6:1 |
| p-vWF 280 mM eluate | 3:1 |

Table 6 shows the stochiometry of vWF:Factor VIII of low and high molecular fractions of plasmic and recombinant vWF. The data show that the low molecular as well as the high molecular fractions of rvWF have a higher binding capacity to Factor VIII than p-vWF.

Example 8: Purification and separation of plasmic vWF, vWF from cryoprecipitate and recombinant vWF Plasmic vWF (p-vWF), vWF from cryoprecipitate (k-vWF) and recombinant vWF (r-vWF) were purified by means of heparin affinity chromatography and the low molecular and high molecular fractions were separated according to Example 1.

Figure 8:
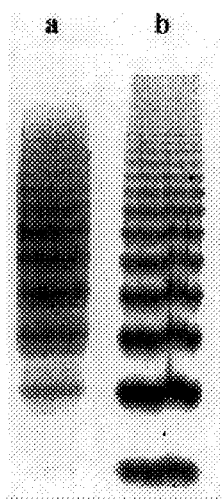
FIG. 8 depicts an electrophoretic analysis of p-vWF and r-vWF after affinity chromatography and elution with 280 NaCl.

From FIG. 7, it is recognizable that the individual fractions of p-vWF and k-vWF have bands which are substantially less sharp than those of r-vWF. This is even more clear in FIG. 8 where the fractionated multimers of p-vWF and r-vWF were directly compared. The sharp bands of r-vWF are clearly visible after separation in the SDS gel, whereas unambiguous intermediates with different molecular weights appear in the fractionation of p-vWF. These "intermediate bands" are traced back to the heterogeneous mixture of differently sized vWF subunits in the p-vWF fractions which arise through digestion with proteases present in plasma. These intermediate products are known in the literature as so-called triplet structures.

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

We claim:

1. A preparation comprising a purified low molecular weight fraction of vWF molecules, wherein the fraction comprises at least 83% vWF-dimers and less than 16% vWF-tetramers and less than 1% higher vWF-multimers.

2. A preparation according to claim 1, wherein the low molecular weight fraction of vWF is obtained from recombinant vWF and the dimers comprise identical vWF subunits.

3. A preparation comprising a purified vWF fraction, wherein the vWF fraction is a high molecular weight fraction comprising at least 80% vWF multimers and the vWF multimers comprise identical subunits.

4. A preparation according to claim 1, wherein the preparation is obtainable by a method comprising absorbing vWF to a heparin affinity support, wherein low molecular weight forms of vWF are eluted at a salt concentration between 150 and 250 mM.

5. A preparation according to claim 1, wherein the preparation does not have platelet aggregation activity.

6. A preparation according to claim 1, wherein the low molecular weight fraction of vWF is obtained from plasma.

7. A preparation comprising a purified vWF fraction, wherein the vWF fraction is a high molecular weight fraction comprising at least 80% vWF multimers and the vWF multimers comprise identical subunits and wherein the preparation has at least 50% higher platelet aggregation activity per microgram protein when compared to the mixture of high molecular weight and low molecular weight vWF fractions, of the starting material from which the high molecular weight vWF was obtained.

8. A preparation according to claim 7, wherein said preparation is obtainable by a method comprising absorbing vWF to a heparin affinity support, wherein high molecular weight forms of vWF are eluted at a salt concentration above 250 mM.

9. A preparation according to claim 8, wherein the fraction comprises at least 80% high molecular weight vWF multimers.

10. A preparation according to claim 7, further comprising a protein having Factor VIII activity.

11. A preparation comprising a purified low molecular weight fraction of vWF, wherein the preparation is obtainable by a method comprising absorbing vWF to a heparin affinity support, wherein low molecular height forms of vWF are eluted at a salt concentration between 150 and 250 mM.

12. A preparation according to claim 11, wherein the low molecular weight fraction comprises at least 83% vWF-dimers and less than 16% vWF-tetramers and less than 1% higher molecular weight vWF-multimers.

13. A preparation according to claim 1, wherein the fraction comprises at least 99% vWF dimers and tetramers.

14. A preparation according to claim 13, wherein the dimers and tetramers comprise identical vWF subunits.

15. A pharmaceutical composition comprising purified high and low molecular weight fractions of vWF, wherein (i) the high and low molecular weight fractions are present in normal physiologic proportions, and (ii) the low molecular weight fraction comprises at least about 83% vWF dimers.

16. A pharmaceutical composition according to claim 15, wherein the composition comprises 35% or less low molecular weight vWF and 65% or more high molecular weight vWF.

17. A pharmaceutical composition according to claim 16, further comprising Factor VIII.

18. A preparation according to claim 3, wherein the preparation is obtainable by a method comprising absorbing vWF to a heparin affinity support, wherein high molecular weight fractions of vWF at salt concentration of at least 250 mM.

19. A preparation according to claim 3, further comprising a protein having Factor VIII activity.

* * * * *